United States Patent [19]
Jeffers

[11] Patent Number: 5,371,467
[45] Date of Patent: Dec. 6, 1994

[54] GAS SENSOR PROBE TIP WITH INTEGRATING FILTER

[76] Inventor: Edward A. Jeffers, 7430 NW 1st Ct., Pembroke Pines, Fla. 33024

[21] Appl. No.: 825,033

[22] Filed: Jan. 24, 1992

[51] Int. Cl.$^5$ .................. G01N 27/60; G01N 31/00
[52] U.S. Cl. ................................ 324/464; 324/455; 73/31.02
[58] Field of Search ............ 324/452, 455, 464, 466; 73/31.07, 31.05, 19.12, 24.06, 25.05, 29.05; 204/176

[56] References Cited

U.S. PATENT DOCUMENTS

| | | | |
|---|---|---|---|
| 3,569,825 | 3/1971 | Lilienfeld | 324/464 |
| 3,970,567 | 7/1976 | Lowther | 204/176 X |
| 4,609,875 | 9/1986 | Jeffers | 324/455 |

*Primary Examiner*—Maura K. Regan
*Attorney, Agent, or Firm*—Malin, Haley, DiMaggio & Crosby

[57] ABSTRACT

An improved corona discharge detection probe, including a corona discharge gas detector, the detector including electronic circuitry, a cathode electrode, an anode electrode spaced from the cathode electrode, and a mechanism for constraining through the probe the flow of atmospheric air to be sensed. The probe has a tip for initially receiving the flow of atmospheric air to be sensed. An external chamber is included, the external chamber being securable to the tip of the detector probe. An adsorbent material is placed within the external chamber about the detector probe such that ambient atmosphere first flows through the chamber prior to encountering the probe tip. The adsorbent material acts to adsorb water vapor in a controlled manner, such that changes in the water vapor level do not affect the detection probe circuitry and thereby eliminates false alarms.

13 Claims, 4 Drawing Sheets

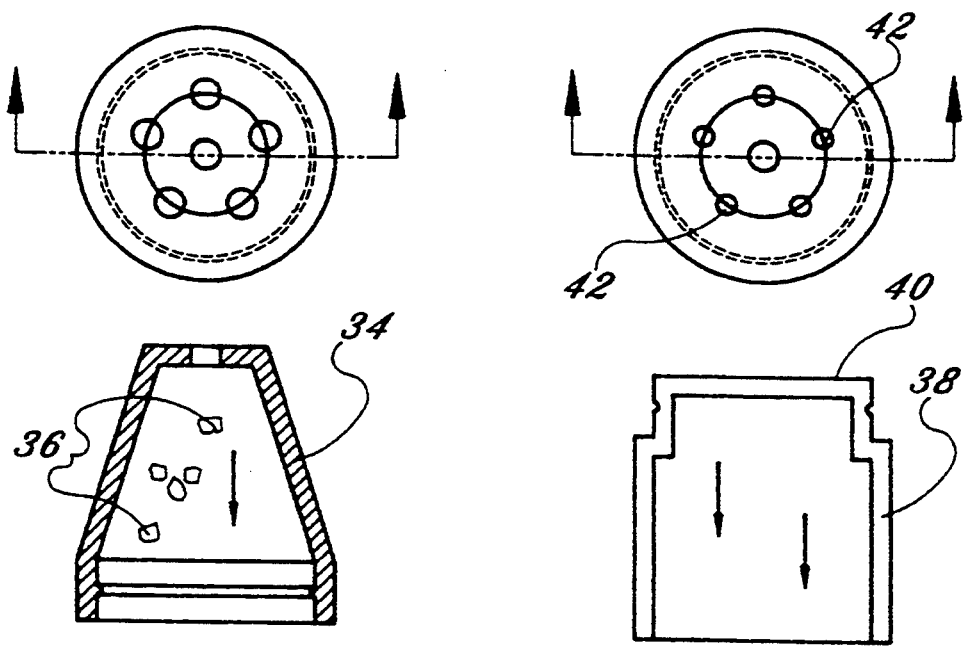
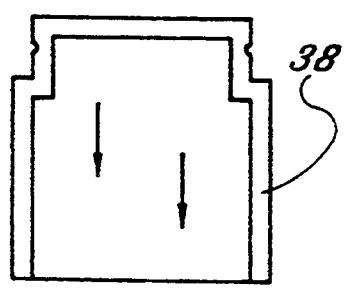
Fig. 7
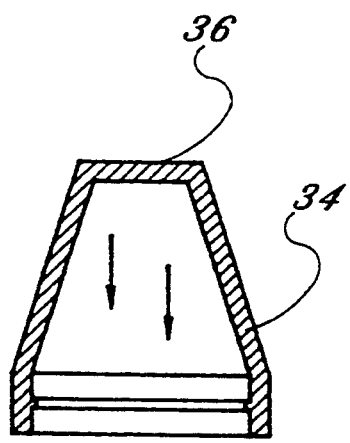
Fig. 5
Fig. 6

GAS SENSOR PROBE TIP WITH INTEGRATING FILTER

BACKGROUND OF THE INVENTION

1. Field of the Invention

This invention relates generally to corona discharge gas sensors and, more particularly, to an improved gas sensor which incorporates an integrating filter for purposes of stabilizing the sensors and eliminating the deleterious effects of water vapor or high humidity regions which impede the detection of leaks.

2. Description of the Prior Art

Refrigerants such as freon are generally utilized in air conditioning and refrigeration systems. In the installation and maintenance of these systems, a method and instrument for detecting gas leakage from the systems was a practical requirement to initially test the proper installation, as well as to maintain the system's operation. Large leaks completely immobilize the units; small leaks gradually decrease the efficiency over time, creating higher operating costs, and ultimately leads to total failure.

There are numerous known methods and devices for conveniently detecting the leakage of small quantities of refrigerant gases into the surrounding atmosphere and the negative corona electrical sensing devices have been found to be superior to other devices. Typically, such halogen or freon gas leak detectors utilize a sensing tip which is projected into the ambient atmosphere zone to be tested or sensed for freon gas contamination indicative of leakage. The sensing tip comprises a small protective shell, constituting the anode electrode, surrounding a point cathode energized by the hand-held body of the instrument to establish a negative corona within the protective shell. Slots or holes provided in the protective shell allow diffusion of the gas molecules into the corona discharge for effecting corona current changes in the presence of freon gas molecules. These current changes activate audio or visual alarms, indicating the presence of atmospheric halogen or gas contamination or leakage to the operator.

U.S. Pat. No. 4,609,875, entitled "Corona Discharge Freon Gas Sensor Having Electrical Wind Pumping Action", and U.S. Pat. No. 4,488,118, entitled "Halogen Gas Leak Detector", disclose sensors utilizing the corona discharge phenomenon to detect leakage. In these devices, electrical circuitry is utilized to produce a high voltage corona, which then reacts to changes in the presence of various gases to produce current changes. Such current changes are then monitored to produce alarm conditions.

Although very sensitive and generally efficient, such corona discharge sensors are also sensitive to water vapor. Condensation in and around air conditioning and refrigerant systems produces areas of high water vapor content relative to areas where there is no condensation or ambient atmosphere. When maintenance personnel or servicemen are searching for leaks, they can quickly move, for example, from an area of 50% relative humidity to one of 90% or higher. When this occurs, modern corona discharge driven detectors are sensitive enough such that they respond to the rapid change in humidity alone and produce a false alarm indication of a leak. That is, the detectors cannot distinguish between corona discharge current being affected by a small refrigerant leak or, alternatively, a rapid change in humidity.

As the CFC and HCFC refrigerant gases generally produce, even in small concentrations, a larger change in the corona discharge current than that affected by the presence of water vapor, servicemen have learned to ignore such false signals. This, of course, leads to human errors in judgment, is an extremely uncertain process, but one that has been generally overlooked by the industry. Also depending upon the size of a refrigerant leak, and its location, it can be impossible to locate the source of the leak when in areas of high water vapor.

This problem has now been compounded by the ozone layer depletion and the use of alternative refrigerants. CFC refrigerants are being replaced with less damaging HFC refrigerants, which are much more benign refrigerants. HFC refrigerants (R-134A) are also much more difficult to sense with a corona discharge detector. Such refrigerants have approximately 4 times less effect on the corona discharge current than do CFC refrigerants of the same concentration. The sensitivity of the detectors can be increased by this factor of 4, however, the detector is then 4 times more sensitive to changes produced by water vapor. This further makes it impossible to distinguish between small concentrations of HFC refrigerant gases and changes in humidity as small as 15%. Preliminary tests have shown that a 15% change in relative humidity will produce the same response from a corona discharge detector as a concentration of 100 parts per million (ppm) of R-134A refrigerant. A concentration of 100 ppm R-134A produces approximately the same response in corona discharge current as does a leak rate standard set at ½ ounce per year.

It is, therefore, highly desirable to provide an improved corona discharge gas detector which overcomes the deficiencies of conventional devices and eliminates false alarm conditions caused by changes in levels of water vapor.

SUMMARY OF THE INVENTION

It is, therefore, an object of this invention to provide a selective filter to be used with a corona discharge leak detector, which eliminates false alarms caused by water vapor.

It is another object of this invention to provide an improved freon or refrigerant gas sensor, which can easily be utilized by modifying previous devices.

It is a further object of this invention to provide an improved freon or refrigerant gas sensor, which is cost-effective, yet operationally efficient.

It is a further object of this invention to provide an improved refrigerant gas sensor, which greatly increases the operation of the modern sensors.

It is a further object of this invention to provide an improved refrigerant gas sensor, which incorporates all of the above-mentioned features and objects.

What is provided is an improved refrigerant gas sensor comprising a housing which incorporates corona discharge circuitry which produces changes in current when encountering freon or refrigerant gases. The improvement lies in modifying the sensor probe or external housing with the addition of a further external chamber placed about the extrememost tip of the probe. The external chamber contains an adsorbing material. The chamber also contains openings which allow for the flow of the ambient atmosphere zone through the external chamber and then is received by the tip of the sensor itself. The adsorbing material acts as an integrating filter to produce a slowly changing humidity level such as to eliminate the sensor indicating a false alarm by water vapor.

Other objects, characteristics, and advantages of the instant invention will become apparent from the following description of specific embodiments.

BRIEF DESCRIPTION OF THE DRAWINGS

The above-mentioned and other features and objects of this invention and the manner of attaining them will become more apparent and the invention itself will be best understood by reference to the following description of embodiments of the invention taken in conjunction with the accompanying drawings, wherein:

FIG. 5 is a longitudinal cross-sectional view of the chamber of FIG. 4 taken along lines 5—5 thereof in the direction of the arrows;

FIG. 6 is a longitudinal cross-sectional view of a portion of FIG. 4 taken along lines 6—6 thereof in the direction of the arrows; and FIG. 7 is a cross-sectional view of the improved chamber of the instant invention in conjunction with the probe interface.

DESCRIPTION OF THE PREFERRED EMBODIMENTS

Figure 1:
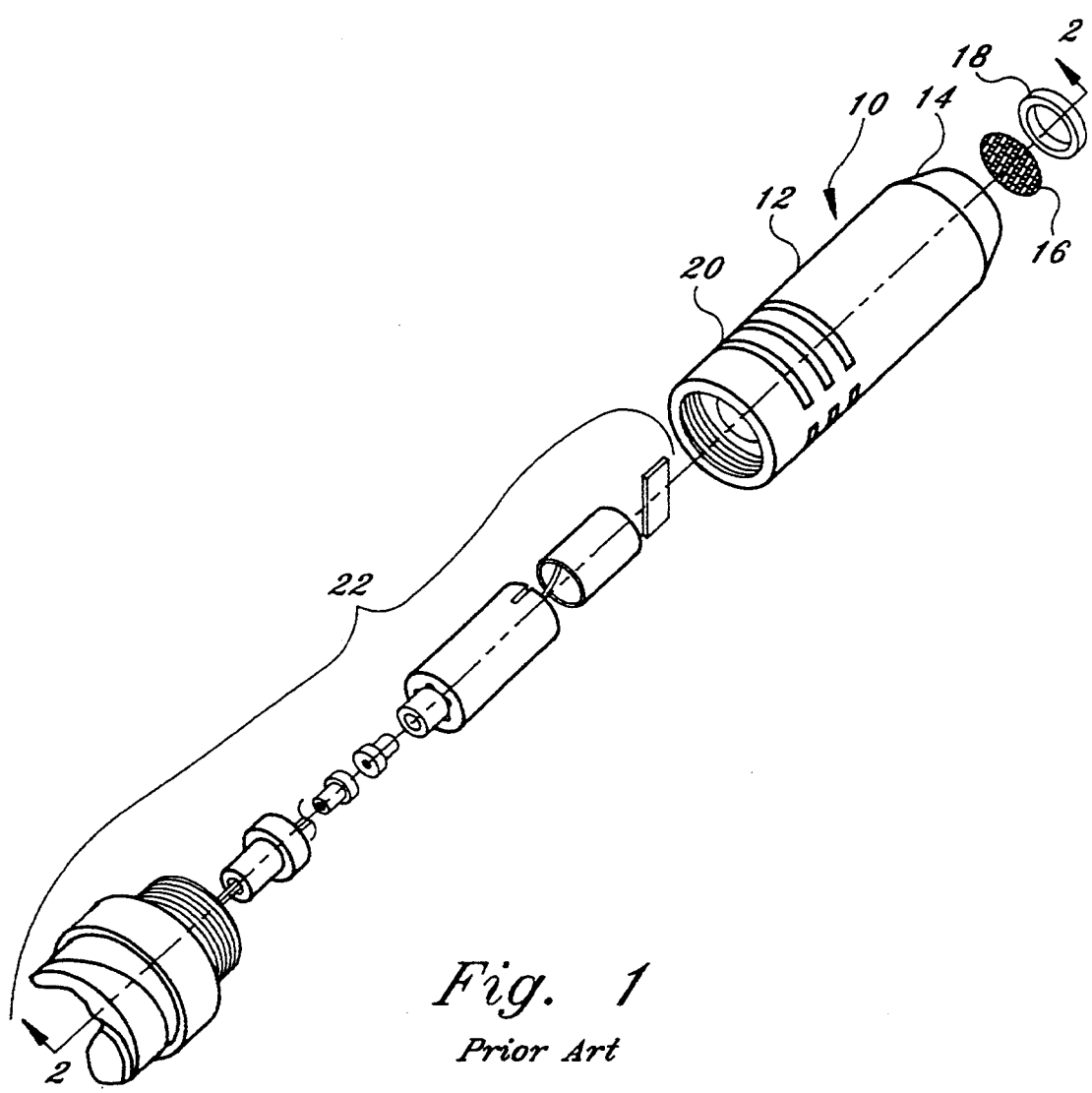
FIG. 1 is an exploded view of a gas sensor probe and portions of the connector fitting.

Referring now to FIG. 1, a sensing tip is illustrated fully at 10. This gas sensor is disclosed in detail in the above-referenced U.S. Pat. No. 4,609,875 and includes a metallic, tubular outer shell 12 which is frusto-conically tapered at 14. The tip includes a wire mesh screen disc 16 secured in place by annular ring 18. A plurality of diametrically opposed transfer slots 20 are cut through the tubular outer shell 12, near the inner end thereof, for discharge flow of the air being sensed for freon or halogen gas contamination. The remaining components 22, as illustrated in FIG. 1, generally house the electronic components including a constraining means and circuitry which are used to produce a high voltage corona discharge as described in detail in U.S. Pat. No. 4,609,875, which teachings are incorporated by reference into this application.

Figure 2A:
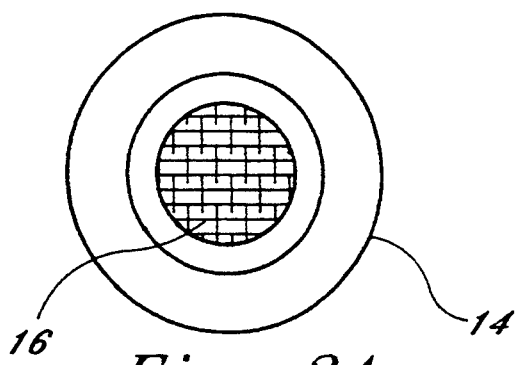
FIG. 2 is a longitudinal cross-sectional view of FIG. 1, taken along the lines 2—2 thereof in the direction of the arrows, illustrating constructional details of the sensing probe.
Figure 2:
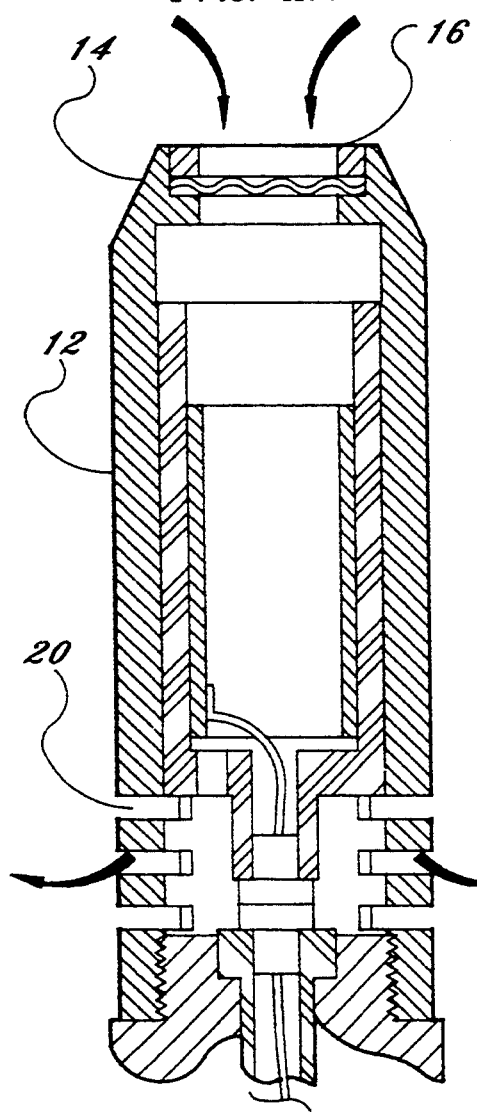

FIG. 2 is a longitudinal cross-sectional view of FIG. 1 along lines 2—2 in assembled condition. Referring to FIGS. 2 and 2A, air flow from the ambient atmosphere enters the tip through screen 16 as indicated by the arrows, flows internally through the tip of the sensing probe 12, and is discharged generally through transverse slots 20 as illustrated.

Figure 3A:
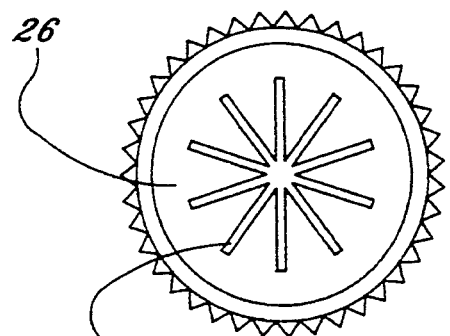
FIG. 3 is a cross-sectional view of an alternative sensing tip.
Figure 3:
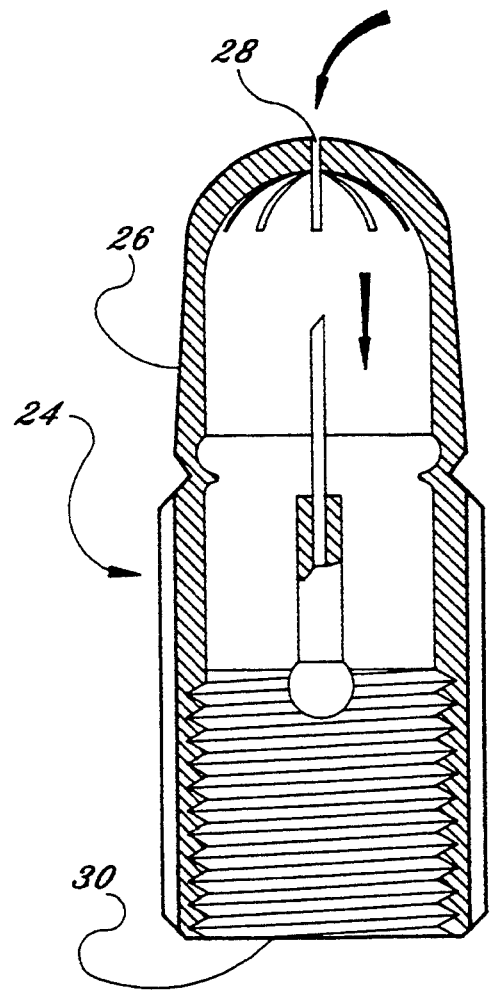

FIGS. 3 and 3A illustrate an alternative conventional sensing tip which details of construction and operation are described in U.S. Pat. No. 4,488,118, whose teachings are hereby incorporated by reference. Probe 24 incorporates a tapered tip 26 which incorporates a plurality of slotted openings 28 to receive the flow of ambient atmosphere. As in other devices, the flow proceeds internally within probe 24 and is discharged through a pump or fan ventilation at 30. It is to be clearly understood that the instant invention has application to both conventional devices with external ventilation, as well as self-ventilation pumping tips.

Figure 4:
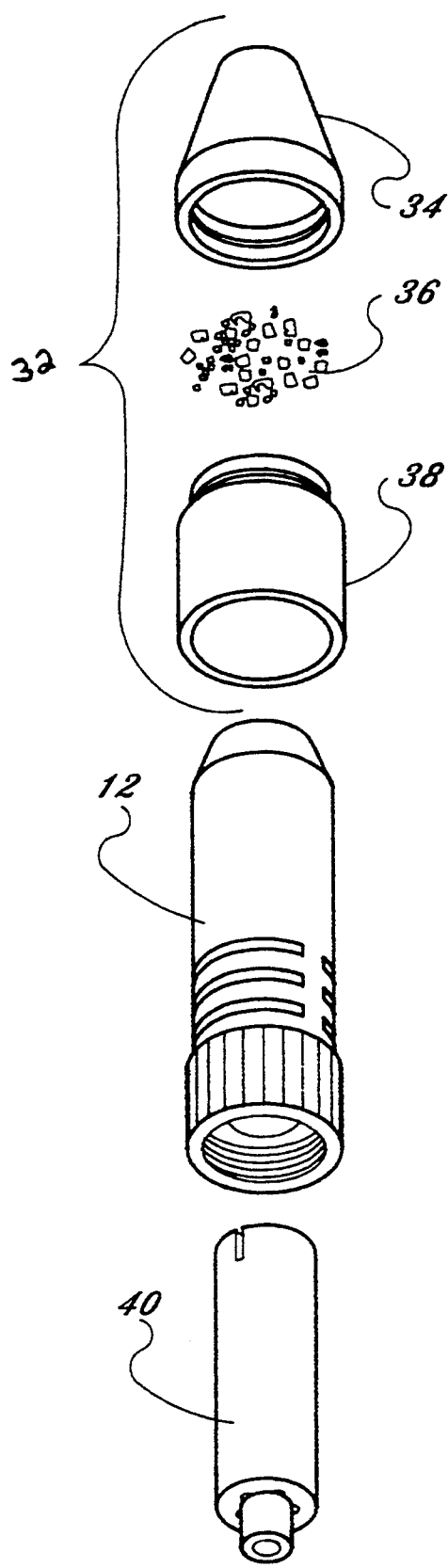
FIG. 4 is an exploded view of the improved sensing probe and portions of the tip connector fittings of the instant invention.

Referring now to FIG. 4, the improvement of the instant invention is generally indicated at 32, being comprised of external chamber housing 34, adsorbent material 36, and probe interface sleeve 38. Probe sensor 12 and internal cartridge 40 are components of the prior art devices as discussed with respect to the U.S. patents cited above.

The instant invention comprises adapting within chamber 34 a calculated quantity of water adsorbing substance 36 which acts as an integrating filter that is positioned in front of, or preceding, a ventilated corona discharge sensor, so as to aspirate the atmosphere containing water vapor and refrigerants through the filter prior to entering the sensor chamber itself. The amount of water vapor adsorbing substance is calculated such that the rate of adsorption, in combination with the aspiration rate and zero balancing characteristics of the electronic detection circuitry, produce a slowly changing, relatively stable humidity atmosphere to which the detector balances itself. The water vapor adsorbing substance is not used to remove water vapor from the atmosphere, but is used as an integrating filter to produce a slowly changing humidity level whose rate of change is less than the zero reference rebalance rate of the detection circuitry.

The precise quantity of material 36 utilized is a matter of design choice dictated by the rebalance rate characteristics of the detection circuity, which is readily apparent to those of ordinary skill in the art. Tests have indicated surprising and startling results in enhancing the operation of the sensing probes. By simply passing a detector above or in proximity to a cup of water, or holding the probe in the palm of the hand, the conventional corona discharge probes would trigger an alarm in the total absence of freon or refrigerant gases. When the instant invention is placed upon the probe, and preceding its internal vents, and the tests are repeated, it immediately eliminates the false alarm conditions in these tests. The same holds true when testing the probe in the vicinity of refrigerant gases wherein the ambient atmosphere also contains varying amounts of water vapor. The improvement eliminates false alarms caused by rapid changes in the water vapor content of the atmosphere with an effectiveness greater than ninety-five percent (95%). The improved device, therefore, practically eliminates the false alarm conditions caused by water vapor which are ordinarily encountered by maintenance personnel.

The adsorbing material 36 has the characteristics to allow the controlled adsorption of moisture as higher levels of humidity are encountered, but then alternatively releases the humidity to the atmosphere when other areas are thereafter encountered with low levels of moisture or water vapor. In this sense, the material is not an "absorbing" material only, but has the tendency to attract, and thereafter release, water vapor at a controlled rate. The material is generally granular and the following examples have proven satisfactory in tests: calcium sulfates, silica gels or other water adsorbing substances.

It is important that material 36 adsorbs moisture faster than the time gradient of the electronic balancing circuity. The corona discharge circuitry initially adjusts to a zero reference or balance point as the unit is turned on and thereafter slowly updates the zero reference.

With the instant chamber housing the adsorbent material preceding the sensor probe tip, the rapid changes in level of water vapor are effectively filtered out, by slowing the rate of change in water vapor content seen by the sensor to a rate which is slower than the rebalance rate of the electronic circuitry, thereby eliminating false alarms.

Whenever the electronic circuitry which drives the corona discharge is enabled, it senses the atmosphere surrounding the sensing tip and balances itself to that atmosphere. Thereafter, changes in the level of refrigerant in the atmosphere are detected and indicated as alarms. In addition, the electronic circuitry continuously rebalances itself relatively slowly to accommodate gradual changes in the atmosphere. The end result of these two actions is to detect only the relatively rapid changes in the level of refrigerant.

The water adsorbing granular material used in this invention operates by taking in (adsorbing) or releasing enough water from the atmosphere around it so as to regulate the rate of change of water vapor seen by the sensor, to a rate less than that of the zero reference updating characteristics of the electronic circuitry. The result of this is that the rate of change in the level of water vapor is integrated or smoothed out such that the rate of change is below that required to produce an output and, therefore, ignored by the instrument. Since the material does not adsorb refrigerant, its level continues to change at a relatively rapid rate and is detected.

Referring now to FIG. 5, a cross-section of the external chamber means 34 is illustrated, which includes tip 36. Tip 36 is constructed with a plurality of circular voids 38 which allow for air flow through the chamber rearwardly towards the probe tip in the direction indicated at the arrows.

FIG. 6 illustrates the probe interface sleeve 38 as having cap end 40. End 40 also has a plurality of circular openings 42 to allow for air flow as herein described.

FIG. 7 illustrates chamber means 34 being placed upon interface sleeve 38 in a snap fit fashion. As will be readily apparent to those skilled in the art, any variety of conventional manufacturing processes can be utilized to attach the chamber means 34 to interface sleeve 38. Granular material 36 is then held within chamber means 34 to initially receive the ambient atmosphere which flows in the direction of the arrows towards the sensor probe tip 14.

In alternative embodiments, the interface sleeve 38 can be eliminated such that the chamber means 34 is fully integrated with, and placed directly upon, probe tip 12. The improvement comprises, in essence, the attachment of an external chamber, housing, and adsorbing material to a sensing probe such that rapid changes in water vapor content of atmosphere are prevented, in a controlled manner, from encountering the corona discharge detection circuitry.

While a specific embodiment of the invention has been shown and described herein for purposes of illustration, it is desired that the protection afforded by any patent which may issue upon this application not be limited strictly to the disclosed embodiment, but that it extend to all structures and arrangements which contain the essence of the invention and which fall within the scope of the claims which are appended hereto. The above descriptions, therefore, are only made by way of example and not as a limitation to the scope of the invention.

What is claimed is:

1. An improved corona discharge detection apparatus for detecting refrigerant leakage, comprising:
   a corona discharge sensing probe having a tip for initially receiving a flow of atmospheric air to be sensed;
   a cathode electrode;
   an anode electrode spaced from said cathode electrode, said cathode electrode and said anode electrode disposed within said sensing probe;
   high voltage corona producing circuitry, said corona producing circuitry electrically connected to said sensing probe, said corona producing circuitry applying an electrical potential to the anode electrode and to the cathode electrode to establish a corona discharge therebetween;
   means for constraining through said sensing probe the flow of atmospheric air to be sensed, said means for constraining disposed within said sensing probe;
   said sensing probe allowing for diffusion of gas molecules within said sensing probe to allow the cathode electrode and the anode electrode in conjunction with the corona producing circuitry to detect refrigerant leakage;
   external chamber means, said external chamber means securable to said tip of said sensor probe; and
   adsorbent material means, said external chamber means housing said adsorbent material, said external chamber means placed about said sensor probe tip such that ambient atmosphere containing water vapor and refrigerants first flows through said external chamber means prior to encountering said sensor probe tip, whereby said adsorbent material acts to adsorb water vapor in a controlled manner, such that changes in said water vapor level do not affect said sensor probe, thereby eliminating false alarms when trying no detect refrigerant leakage.

2. The apparatus of claim 1, wherein said external chamber means further includes interface sleeve means, said interface sleeve means being interposed between said probe tip and said external chamber means.

3. The apparatus of claim 2, wherein said external chamber means comprises a tapered housing, said tapered housing terminating at one end, said end having a plurality of voids allowing for the flow of said ambient atmosphere; said interface sleeve comprising a cylindrical sleeve terminating at one end, said end having a plurality of voids allowing for the flow of said ambient atmosphere, said adsorbent material being placed within said tapered chamber.

4. An improved corona discharge detection apparatus for detecting refrigerant leakage, comprising:
   a corona discharge sensing probe having a tip for initially receiving a flow of atmospheric air to be sensed;
   a cathode electrode;
   an anode electrode spaced from said cathode electrode, said cathode electrode and said anode electrode disposed within said sensing probe;
   high voltage corona producing circuitry, said corona producing circuitry electrically connected to said sensing probe, said corona producing circuitry applying an electrical potential to the anode electrode and to the cathode electrode to establish a corona discharge therebetween;
   means for constraining through said sensing probe the flow of atmospheric air to be sensed, said means for constraining disposed within said sensing probe;

said sensing probe allowing for diffusion of gas molecules within said sensing probe to allow the cathode electrode and the anode electrode in conjunction with the corona producing circuitry to detect refrigerant leakage;

external chamber means, said external chamber means securable to said tip of said sensor probe; and adsorbent material means, said external chamber means housing said adsorbent material, said external chamber means placed about said sensor probe tip such that ambient atmosphere first flows through said chamber means prior to encountering said sensor probe tip, said adsorbing material acting as an integrating filter to produce a slowly changing humidity level to eliminate said sensor probe indicating a false alarm by water vapor when trying to detect refrigerant leakage.

5. The apparatus of claim 3, wherein said external chamber means further includes interface sleeve means, said interface sleeve means being interposed between said probe tip and said external chamber means.

6. The apparatus of claim 5, wherein said external chamber means comprises a tapered housing, said tapered housing terminating at one end, said end having a plurality of voids allowing for the flow of said ambient atmosphere; said interface sleeve comprising a cylindrical sleeve terminating at one end, said end having a plurality of voids allowing for the flow of said ambient atmosphere, said adsorbent material being placed within said tapered chamber.

7. The apparatus of claim 4, wherein said adsorbent material means has an aspiration rate and said electronic circuitry has zero balancing characteristics, whereby an amount of adsorbent material means to be placed within said external chamber means is chosen such that the rate of adsorption, in combination with the aspiration rate and zero balancing characteristics, produces a slowly changing, relatively stable humidity atmosphere to which said sensor probe balances itself.

8. The apparatus of claim 4 wherein said adsorbing material allows for controlled adsorption of moisture as higher levels of humidity are encountered, but then alternatively releases the humidity to the atmosphere when other areas are thereafter encountered with low levels of moisture or water vapor.

9. The apparatus of claim 4, wherein said adsorbing material adsorbs moisture faster than the electronic balancing circuitry.

10. An improved corona discharge detection apparatus for detecting refrigerant leakage comprising:

a corona discharge sensing probe having a tip for initially receiving a flow of atmospheric air to be sensed;

a cathode electrode;

an anode electrode spaced from said cathode electrode, said cathode electrode and said anode electrode disposed within said sensing probe;

high voltage corona producing circuitry, said corona producing circuitry electrically connected to said sensing probe, said corona producing circuitry applying an electrical potential to the anode electrode and to the cathode electrode to establish a corona discharge therebetween;

means for constraining through said sensing probe the flow of atmospheric air to be sensed, said means for constraining disposed within said sensing probe;

said sensing probe allowing for diffusion of gas molecules within said sensing probe to allow the cathode electrode and the anode electrode in conjunction with the corona producing circuitry to detect refrigerant leakage;

external chamber means, said external chamber means securable to said tip of said sensor probe; and adsorbent material means, said external chamber means housing said adsorbent material, said external chamber means placed about said sensor probe tip such that ambient atmosphere first flows through said chamber means prior to encountering said sensor probe tip, said adsorbent material eliminating the effects of water vapor on said sensor probe without eliminating the water vapor itself by slowing the rate of change in water vapor content seen by said sensor probe to a rate which is slower than the rebalance rate of said electronic circuitry, such that changes in said water vapor level do not affect said sensor probe, thereby eliminating false alarms when trying to detect refrigerant leakage.

11. The apparatus of claim 10, wherein said adsorbent material means has an aspiration rate and said electronic circuitry has zero balancing characteristics, whereby an amount of adsorbent material means to be placed within said external chamber means is chosen such that the rate of adsorption, in combination with the aspiration rate and zero balancing characteristics, produces a slowly changing, relatively stable humidity atmosphere to which said sensor probe balances itself.

12. The apparatus of claim 10 wherein said adsorbing material allows for controlled adsorption of moisture as higher levels of humidity are encountered, but then alternatively releases the humidity to the atmosphere when other areas are thereafter encountered with low levels of moisture or water vapor.

13. The apparatus of claim 10 wherein said adsorbing material adsorbs moisture faster than the electronic balancing circuitry.

* * * * *